United States Patent [19]

Law et al.

[11] 4,306,863
[45] Dec. 22, 1981

[54] AMALGAM DISPENSER WITH LOCKABLE PLUGGER

[75] Inventors: Franklin E. Law, Adelphi, Md.;
Hazel Harper, 2139 Georgia Ave., NW., Washington, D.C. 20001

[73] Assignee: Hazel J. Harper

[21] Appl. No.: 201,620

[22] Filed: Oct. 28, 1980

[51] Int. Cl.³ .............................................. A61C 3/08
[52] U.S. Cl. .................................................... 433/83
[58] Field of Search ..................... 433/90, 164, 83, 89

[56] References Cited

U.S. PATENT DOCUMENTS 1,797,866  3/1931  Ivory .
2,352,808  7/1944  Siqueland ............................ 433/83
2,503,156  4/1950  Ivory .
2,679,102  5/1954  Ivory, Jr. .

Primary Examiner—Robert Peshock
Attorney, Agent, or Firm—Lane, Aitken, Kice & Kananen

[57] ABSTRACT

A dental implement for dispensing and compacting amalgam includes separate dispensing and compacting assemblies at opposite ends of a handle. The assemblies each have an amalgam carrier cooperating with a plugger portion which extends from an end of the handle. A spring-biased lever maintains the amalgam carrier in a normally lowered position capable of receiving amalgam. Each assembly features a lock for releasably retaining the amalgam carrier in a raised position whereby the plugger portion extends beyond its respective amalgam carrier for tamping the amalgam into a tooth cavity.

10 Claims, 9 Drawing Figures

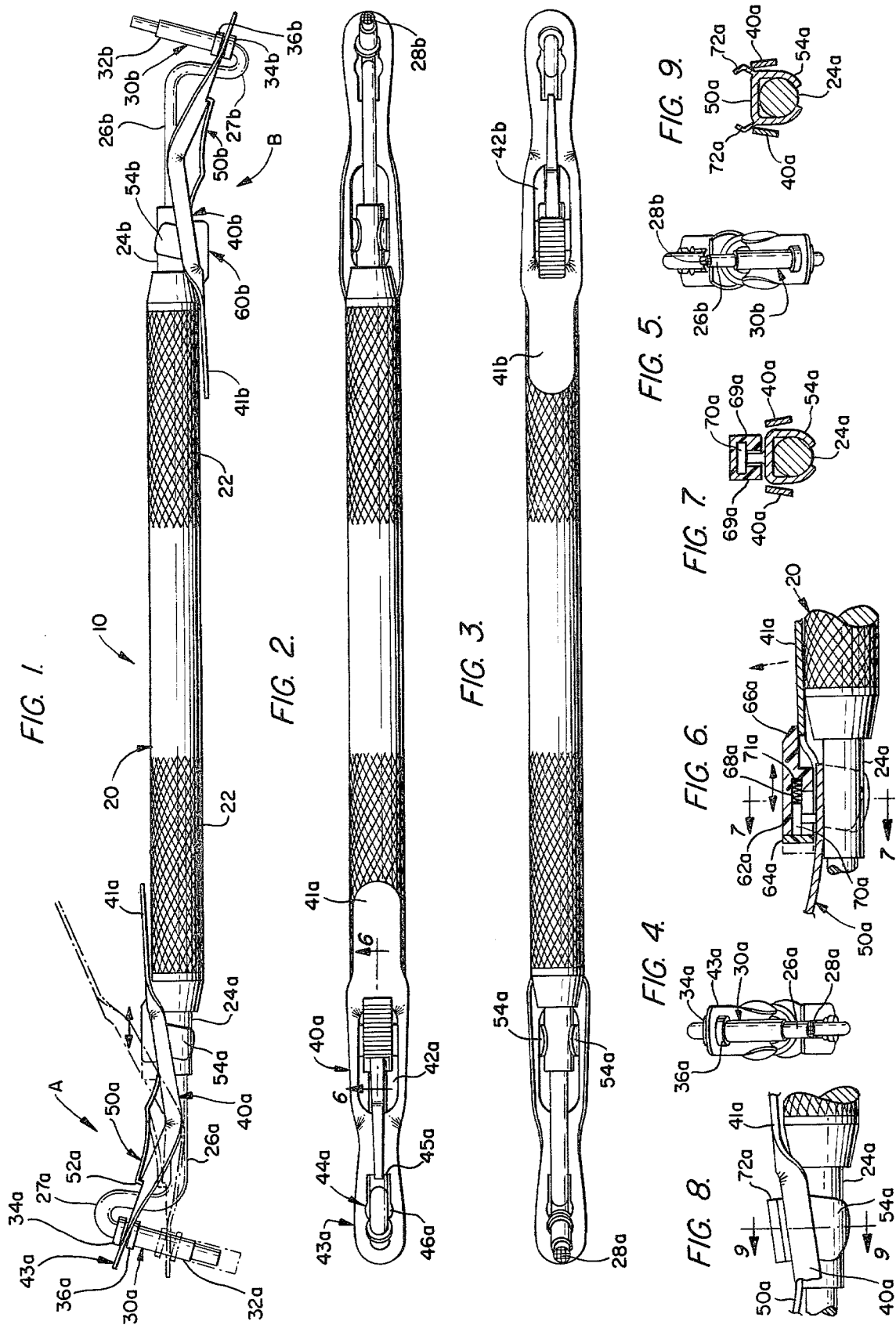

AMALGAM DISPENSER WITH LOCKABLE PLUGGER

BACKGROUND OF THE INVENTION

This invention relates to a dental implement for dispensing and compacting amalgam into a tooth cavity. It concerns, more particularly, an amalgam dispenser adapted to be locked with the plugger or amalgam tamper in an extended position so that the implement may be used to condense the filling.

Conventionally, the dentist has used an amalgam dispenser in filling a patient's cavity and then another dental implement was used to compact the amalgam to the proper degree of firmness. From a practical standpoint, this procedure was both time consuming and inconvenient. To avoid the inconvenience of changing dental instruments, the disclosure of an amalgam carrier in U.S. Pat. No. 1,797,866, issued Mar. 24, 1931, to C. S. Ivory, suggests at page 2, lines 47–65, that the dispenser also may be used to pack the amalgam into the cavity. This is accomplished by depressing a spring-actuated lever which raises a tubular amalgam carrier on a plunger shaft thereby dispensing the amalgam into the cavity. By maintaining the lever in the lowered position the plunger remains extended beyond the end of the tubular carrier. Provided the dental practitioner's finger is not released, the plunger may be used to tamp the amalgam. Although the device represents an improvement over the practice of using a separate dental implement for the compacting operation, it requires the practitioner to first, physically hold the lever in a particular lowered position and second, adopt a grip on the implement that maintains the lever in the lowered position while at the same time permitting a workable compacting motion. Thus, in practice, hand movement is restricted and the compacting process becomes cumbersome and time consuming.

SUMMARY OF THE INVENTION

It is, therefore, an object of the present invention to improve the compacting operation by providing an amalgam dispenser including an amalgam carrier which is adapted to automatically lock in a raised position whereby a portion of the plugger remains extended from the carrier.

It is a further object of the present invention to provide in a single dental implement twin amalgam dispensing and compacting assemblies, one having a larger amalgam carrier and plugger portion than the other, so that the amount of amalgam dispensed and subsequently compacted can be readily adjusted to meet the filling and condensing requirements of the particular tooth cavity.

Toward the fulfillment of these objectives, the dental implement of the present invention includes a handle having reduced plugger or amalgam condensing portions extending from either end of the handle. Operatively mounted on each end of the implement are amalgam dispensing and compacting assemblies. Each assembly includes a tubular amalgam carrier engaging a finger operated lever to which a spring is connected for maintaining the lever in a normally raised position. Each assembly features a slip-fit lock adapted to reciprocate parallel to the longitudinal axis of the handle for automatically and releasably engaging the lever to lock the amalgam carrier in a raised position thereby exposing a portion of the plugger beyond the end of the carrier. In an alternate embodiment, each assembly employs spring detent members to lock the carrier in a raised position.

In use, a suitable amount of amalgam is placed in one amalgam carrier. With the implement held in position adjacent the tooth cavity the lever is depressed raising the carrier on the plugger portion thereby releasing the amalgam. The implement is immediately changed to its compacting mode when the slip fit lock automatically slides to the rear so that the rearwardly extending flange of the lock overlaps the finger piece of the lever causing the lever to remain close against the handle. In this position the amalgam carrier has been lifted on the plugger portion and the end of the plugger portion is extended for compacting the amalgam. In the alternate embodiment, the finger piece is forced past the spring detent members and is then retained adjacent the handle by the spring detent members.

BRIEF DESCRIPTION OF THE DRAWINGS

FIG. 1 is a side elevational view of the amalgam dispenser with lockable plugger according to the present invention.

FIG. 2 is a top view of the amalgam dispenser of FIG. 1.

FIG. 3 is a bottom view of the amalgam dispenser of FIG. 1.

FIG. 4 is a left end view of the amalgam dispenser of FIG. 1.

FIG. 5 is a right end view of the amalgam dispenser of FIG. 1.

FIG. 6 is an enlarged fragmentary sectional view taken along the lines 6—6 of FIG. 2.

FIG. 7 is an enlarged sectional view taken along the lines 7—7 of FIG. 6.

FIG. 8 is an enlarged fragmentary side elevational view of the amalgam dispenser employing an alternate locking mechanism.

FIG. 9 is a sectional view taken along the lines 9—9 of FIG. 8.

DESCRIPTION OF THE PREFERRED EMBODIMENT

In FIG. 1, reference character 10 refers to the amalgam dispenser with lockable plugger in accordance with the present invention. A handle 20 connects and supports at opposite ends thereof two amalgam dispensing and compacting assemblies designated in general by the reference characters A and B respectively.

The handle 20 may be engraved with diagonal grooves of shallow depth as shown at 22 to aid in gripping the dental instrument. The handle 20 tapers at both ends to rounded front portions 24a and 24b. The front portions 24a and 24b each have a central bore for receiving reduced diameter rods or plugger portions 26a and 26b respectively. The plugger portions 26a and 26b curve, then extend outwardly from front portions 24a and 24b, respectively, along the longitudinal axis of the handle 20. The forward end of each plugger portion 26a and 26b bends upwardly until at 27a and 27b, respectively, the plugger portions 26a and 26b curve, then extend downwardly terminating in serrated tips 28a and 28b as shown in FIGS. 2 and 3.

Amalgam dispensing and compacting assemblies A and B are inverted with respect to one another, as shown in FIG. 1, for ease of handling during the dispensing and compacting operation. Assembly A provides a larger amalgam carrying capacity than assembly B although the operation and elements of each, exclusive of small dimensional variations, are identical. In this regard, assembly A will be described with the understanding that the description applies likewise to assembly B. Amalgam dispensing and compacting assembly A includes an amalgam carrier 30a, a lever member 40a, a spring 50a and a slip-fit lock 60a.

The amalgam carrier 30a comprises a tubular member 32a provided with upper and lower flanges 34a and 36a, respectively, spaced apart from one another. When the lever member 40a is in its normally raised position, shown in broken lines in FIG. 1, the amalgam carrier 30a is in its normally lowered position, also shown in broken line perspective. The space between the tip 28a of the plugger portion 26a and the end of the tubular member 32a forms a chamber for receiving a suitable amount of amalgam for subsequent dispensing into the dental cavity. The cross-sectional diameter of the tubular member 32a is somewhat greater than that of the corresponding tubular member 32b of the amalgam carrier 30b, hence, the dental practitioner may select the amalgam dispensing and compacting assembly to dispense an amount of amalgam that will more closely conform to the requirements of the patient's cavity. Also, the tip 28b of the plugger portion 26b has a correspondingly smaller cross-sectional surface area than the tip 28a and, as such, is more suited to packing the amalgam in small dental recesses.

The lever member 40a includes a rear finger piece 41a which is cut out, as indicated at 42a of FIG. 2, to clear the rear portion of the spring 50a. The front end of the lever 40a ends in a flat portion 43a which includes a slot 44a. The slot 44a has a rear wall 45a, a central enlarged opening 46a and reduced end openings for receiving the amalgam carrier 30a. The upper and lower flanges 34a and 36a, respectively, of the amalgam carrier 30a are of such a diameter that they pass through the central enlarged opening 46a but not through the reduced end openings. In this way, the front end of the flat portion 43a engages the amalgam carrier 30a between the upper and lower flanges 34a and 36a. When the finger piece 41a of the lever 40a is depressed, as shown in FIG. 1, from the normally raised position to the lowered position adjacent the handle 20, the flat portion 43a exerts an upward force on the upper flange 34a. Consequently, the amalgam carrier 30a is raised and the plugger portion 26a extends beyond the end of tubular member 32a.

The flat spring 50a keeps the amalgam carrier 30a in a normally lowered position capable of receiving amalgam in the open chamber. As depicted in FIGS. 1 and 2, the flat spring 50a includes at its forward end a downwardly-depending lip 52a that engages the rear wall 45a of the slot 44a. The spring 50a has a rear portion including downwardly-depending clips 54a which snap or slide over the rounded front portion 24a of the handle 20. The rear portion of the spring 50a may be further secured to the handle 20 by a screw (not shown) extending through the top of the rear portion of the spring 50a into the top of the rounded front portion 24a of the handle 20. It will be understood that conventional soldering techniques may be used to secure the top of the rear portion of the spring 50a to the handle 20 and, if this approach is followed, the downwardly-depending clips 54a of the spring 50a may be eliminated.

In FIG. 1, the slip-fit lock designated generally as 60a, coacts with the finger piece 41a of the lever 40a to retain the lever 40a in the lowered position adjacent the handle 20. As depicted in FIG. 6, the slip-fit lock 60a includes a central body portion 62a, a closure cap 64a and a rear overhanding flange 66a having an upwardly facing bevelled cam surface 67a. As depicted in FIGS. 6 and 7, the body portion 62a has an interior longitudinal channel 68a formed by side walls 69a thereof. A retainer pin 70a is secured through the top surface of the rear portion of the spring 50a extending generally perpendicular to the top surface of the handle 20. The closure cap 64a is soldered or otherwise attached to the front end of the body portion 62a after the slip-fit lock 60a is slideably mounted on the pin 70a. A spring 71a is retained in the channel 68a between the pin 70a and the rear end of the channel 68a to bias the slip-fit lock 60a rearwardly toward the finger piece 41a. Although the spring 71a is depicted as a coil spring, it is understood that other types of springs may be employed. For example, a small pad of a resilient elastomeric material may be used in the channel 68a. In this manner, the slip-fit lock 60a is adapted to reciprocate along the length of the channel 68a for releasably retaining the lever 40a. To accomplish this, the rear portion of the cut-out portion 42a engages the bevelled cam surface 67a to cam the slip-fit lock 60a forward, so that the finger piece 41a can move past the rear overhanging flange 66a and into its lowered position adjacent the handle 20. When the finger piece 41a is in its lowered position, the spring 71a biases the slip-fit lock to its rear position in which the rear overhanging flange 66a is positioned over the front portion of the finger piece 41a, thereby holding the lever 40a in proximity to the handle 20. When the flange 66a engages the finger piece 41a, the plugger portion 26a is maintained in an extended position beyond the end of the carrier 30a.

In operation, the appropriate amalgam dispensing and compacting assembly is selected depending on the amount of amalgam required for the patient's cavity. Assume that the patient has a large cavity. A large cavity would of necessity require a greater amount of amalgam; consequently, the larger assembly A would be filled. While the amalgam carrier 30a is being filled, the lever 40a is raised. Assembly A is inserted into the patient's mouth to begin the dispensing and compacting procedure. By depressing the finger piece 41a, the amalgam carrier 30a rises due to the flat portion 43a of the lever 40a pushing upwardly on the upper flange 34a. As the amalgam carrier 30a is lifted, the serrated tip 28a of the plugger portion 26a acts against the amalgam in the chamber to force it into the tooth cavity. At the end of the dispensing stroke, the slip-fit lock 60a is biased rearwardly by the spring 71a so that the rear flange 66a lies on top of the finger piece 41a to lock the lever 40a close to the handle 20. This maintains the amalgam carrier 30a in a raised position with a portion of the plugger 26a extended as shown in FIG. 4. The serrated tip 28a of the plugger portion 26a is then used to tamp the amalgam into the cavity. If a smaller tamping implement is required during the compacting process, the smaller plugger 26b, as shown extended in FIG. 5, may be used.

An alternate form of locking mechanism, as illustrated in FIGS. 8 and 9, is contemplated for use with the dental implement in accordance with the present invention. A pair of V-shaped spring detent members 72a each comprising an upper angled leg and lower angled leg are connected to the rear end of the spring 50a. The edge of one leg of each detent member is attached to or integrally formed with a lateral edge of the rear end of the spring 50a, so that the point of the V is directed laterally outward, extending beyond the edge of the spring 50a into the path of travel of the finger piece 41a and interfering with the movement of the finger piece 41a. Upon downward movement of the finger piece 41a, the sides of the cut-out portion 42a of the finger piece 41a engage the upper angled legs of each spring detent member 72a. Further downward movement of the finger piece 41a causes the deflection of the spring detent members 72a laterally inward against the resiliency of the spring material. When the finger piece 41a has travelled down past the point of the V, the spring detent members 72a move outward, with the lower angled legs extending over the sides of the cut-out portion 42a and holding the finger piece 41a down adjacent the handle 20. The spring detent members 72a have sufficient stiffness to resist the upward bias exerted on the finger piece 41a by the spring 50a. In order to be released from its lower position, the finger piece 41a must be manually forced up past the spring detent members 72a.

While the invention has been described in the context of two specific locking assemblies, i.e., the slip-fit lock 60a and the spring detent members 72a, illustrated in the drawings, it will be appreciated by those skilled in the art that other suitable locking means may be used to retain the lever 40a in a locked position adjacent the handle 20. For example, a slip ring that is reciprocable along the length of the handle 20 could be used to overlap and secure either finger piece 41a or 41b. Such modifications do not depart from the concept manifested by the illustrated embodiment. Accordingly, it is expressly intended that the foregoing description is illustrative of a preferred embodiment only, not limiting, and that the true spirit and scope of the present invention be determined by reference to the appended claims.

What is claimed is:

1. In a dental implement for dispensing amalgam, said implement having a handle, a lever mounted on said implement, an amalgam carrier engaging the lever, a reduced plugger portion extending from one end of the handle and cooperating with the amalgam carrier to dispense the amalgam, a spring having a rear end secured to the handle and a front end engaging the lever to maintain the carrier in a normally lowered position so that by operating the lever the amalgam carrier is raised and the plugger portion extends beyond the amalgam carrier, thereby acting to discharge the amalgam, the improvement comprising:

means for retaining said lever in a locked position in proximity to the surface of said handle with said amalgam carrier raised, so that said plugger portion extends beyond said amalgam carrier whereby said plugger portion may be used to compact the amalgam.

2. The dental implement of claim 1 wherein the retaining means comprises means for automatically interlocking with the lever.

3. The dental implement of claim 1 wherein said retaining means comprises a slip-fit lock including:
a body portion adapted to reciprocate in a longitudinal direction parallel to the axis of said handle for releasably engaging said lever.

4. The dental implement of claim 1 wherein said retaining means comprises a slip-fit lock including:
a pin mounted on the dental implement and extending through said rear end of said spring, and
a body portion having a channel therein for receiving said pin so that said slip-fit lock is reciprocable along said channel.

5. The dental implement of claim 3 or claim 4 wherein the body portion includes a cam surface engageable by said lever to move said slip-fit lock so that the lever can move past the body portion, and means for biasing the slip-fit lock into engagement with the lever.

6. The dental implement of claim 4 wherein said slip-fit lock further comprises:
said channel being open at one end, and
a closure cap secured to said body portion, closing said channel and thereby retaining said pin within said body portion.

7. The dental implement of claim 6 wherein said slip-fit lock further comprises:
a flange extending rearwardly from said body portion for engaging said lever as said slip-fit lock slides into locking position.

8. The dental implement of claim 1 wherein said retaining means comprises at least one spring detent member extending into the path of travel of the lever and interfering with the movement of said lever.

9. The dental implement according to claim 8 wherein the spring detent member is mounted on said spring.

10. The dental implement of claim 1 wherein said retaining means comprises a pair of detent members engageable with said lever.

* * * * *